(12) United States Patent
Acker et al.

(10) Patent No.: US 6,453,190 B1
(45) Date of Patent: *Sep. 17, 2002

(54) MEDICAL PROBES WITH FIELD TRANSDUCERS

(75) Inventors: David E. Acker, Setauket, NY (US); Yaniv Bejerano, Haifa (IL)

(73) Assignee: Biosense, Inc., New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,802
(22) PCT Filed: Feb. 14, 1997
(86) PCT No.: PCT/US97/02443
  § 371 (c)(1),
  (2), (4) Date: Dec. 10, 1998
(87) PCT Pub. No.: WO97/29710
  PCT Pub. Date: Aug. 21, 1997

Related U.S. Application Data
(60) Provisional application No. 60/011,743, filed on Feb. 15, 1996, provisional application No. 60/011,723, filed on Feb. 15, 1996, and provisional application No. 60/017,635, filed on May 17, 1996.

(30) Foreign Application Priority Data
  Sep. 17, 1996 (IL) .................................................. 119262

(51) Int. Cl.[7] .............................................. A61B 19/00
(52) U.S. Cl. ....................... 600/424; 128/897; 128/899; 340/686.1
(58) Field of Search ................................. 600/424, 425; 128/897, 899; 606/130; 340/686; 356/375, 614

(56) References Cited

U.S. PATENT DOCUMENTS

| 3,644,825 A | 2/1972 | Davis et al. ................... 324/41 |
| 3,868,565 A | 2/1975 | Kaipers ..................... 324/34 R |

(List continued on next page.)

FOREIGN PATENT DOCUMENTS

| WO | WO 94/00050 | 1/1994 |
| WO | WO 94/04938 | 3/1994 |
| WO | WO 94/06349 | 3/1994 |
| WO | WO 94/23647 | 10/1994 |
| WO | WO 94/28782 | 12/1994 |
| WO | WO 95/05773 | 3/1995 |

(List continued on next page.)

OTHER PUBLICATIONS

"Effects of laser irradiation delivered by flexible fiberoptic system on the left venticular internal myocardium" American Heart Journal, Sep. 1983, pp. 587–590.
Dorothy Bonn, "High–Power laser help the Ischaemic Heart", The Lancet, vol. 348 (Jul. 13, 1996) p. 118.
Mahmood Mirhoseini et al. "Transmyocardial Laser Revascularization: A Review" Journal of Clinical Laser Medicine & Surgery. vol. 11(1993)pp. 15–19.

*Primary Examiner*—Ruth S. Smith
(74) *Attorney, Agent, or Firm*—Louis J. Capezzuto (57) ABSTRACT

A field transducer (30) for determining position or orientation in a medical instrument locating system is placed at an arbitrary position or orientation with respect to a feature (62) of the instrument (46). The transducer (30) may be attached at a arbitrary location on the instrument (46), or the instrument (400, 404) may be bent as desired by the user. A transform relating position or orientation of feature of the instrument to position or orientation of the tranducer is obtained in a caliration cycle. A field transducer may be part of a disposable unit which is irrevocably altered when used with an instrument so that the unit cannot be reused.

12 Claims, 6 Drawing Sheets

U.S. PATENT DOCUMENTS

| | | | |
|---|---|---|---|
| 4,017,858 A | 4/1977 | Kaipers | 343/100 R |
| 4,054,881 A | 10/1977 | Raab | 343/112 R |
| 4,560,930 A | 12/1985 | Kouno | 324/207 |
| 4,570,354 A | 2/1986 | Hindes | 33/534 |
| 4,592,356 A | 6/1986 | Guiterrez | 128/339 |
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,788,987 A | 12/1988 | Nickel | 128/777 |
| 4,849,692 A | 7/1989 | Blood | 324/208 |
| 4,869,238 A | 9/1989 | Opie et al. | 128/6 |
| 4,905,698 A | 3/1990 | Strohl, Jr. et al. | 128/653 R |
| 4,917,095 A | 4/1990 | Fry et al. | 128/660.03 |
| 4,921,482 A | 5/1990 | Hammerslag et al. | 604/95 |
| 4,931,059 A | 6/1990 | Markham | 606/185 |
| 4,945,305 A | 7/1990 | Blood | 324/207.117 |
| 5,002,137 A | 3/1991 | Dickinson et al. | 175/19 |
| 5,042,486 A | 8/1991 | Pfeiler et al. | 128/653 R |
| 5,059,197 A | 10/1991 | Urie et al. | 604/164 |
| 5,078,144 A | 1/1992 | Sekino et al. | 128/660.03 |
| 5,099,845 A | 3/1992 | Besz et al. | 128/653.1 |
| 5,125,924 A | 6/1992 | Rudko | 606/12 |
| 5,125,926 A | 6/1992 | Rudko et al. | 606/19 |
| 5,158,084 A | 10/1992 | Ghiatas | 128/657 |
| 5,172,056 A | 12/1992 | Voision | 324/207.17 |
| 5,195,540 A | 3/1993 | Shiber | 128/898 |
| 5,195,968 A | 3/1993 | Lundquist et al. | 604/95 |
| 5,197,482 A | 3/1993 | Rank et al. | 128/749 |
| 5,211,165 A | 5/1993 | Dumoulin et al. | 128/653.1 |
| 5,215,680 A | 6/1993 | D'Arrigo | 252/307 |
| 5,217,484 A | 6/1993 | Marks | 606/200 |
| 5,234,426 A | 8/1993 | Rank et al. | 606/1 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,267,960 A | 12/1993 | Hayman et al. | 604/106 |
| 5,273,025 A | 12/1993 | Sakiyama et al. | 128/6 |
| 5,275,166 A | 1/1994 | Vaitekunas et al. | 128/660.03 |
| 5,295,484 A | 3/1994 | Marcus et al. | 128/660 |
| 5,295,486 A | 3/1994 | Wollschager et al. | 128/661.01 |
| 5,301,682 A | 4/1994 | Debbas | 128/737 |
| 5,309,913 A | 5/1994 | Kormos et al. | 128/653 |
| 5,325,873 A | 7/1994 | Hirschi et al. | 128/899 |
| 5,368,564 A | 11/1994 | Savage | 604/95 |
| 5,368,592 A | 11/1994 | Stern et al. | 128/662 |
| 5,375,596 A | 12/1994 | Twiss et al. | 128/653.1 |
| 5,377,678 A | 1/1995 | Dummoulin et al. | 128/653.1 |
| 5,380,316 A | 1/1995 | Aita et al. | 606/7 |
| 5,383,454 A | 1/1995 | Bucholz | 128/653.1 |
| 5,383,874 A | 1/1995 | Jackson et al. | 606/1 |
| 5,383,923 A | 1/1995 | Webster, Jr. | 607/125 |
| 5,385,148 A | 1/1995 | Lesh et al. | 128/662.06 |
| 5,389,096 A | 2/1995 | Aita et al. | 606/15 |
| 5,391,199 A | 2/1995 | Ben Haim | 607/122 |
| 5,403,356 A | 4/1995 | Hill et al. | 607/14 |
| 5,404,297 A | 4/1995 | Birk et al. | 362/421 |
| 5,409,004 A | 4/1995 | Sloan | 128/657 |
| 5,423,321 A | 6/1995 | Fontenot | 128/664 |
| 5,425,367 A | 6/1995 | Shapiro et al. | 128/653 |
| 5,425,382 A | 6/1995 | Golden et al. | 128/899 |
| 5,429,132 A | 7/1995 | Guy et al. | 128/653.1 |
| 5,431,168 A | 7/1995 | Webster, Jr. | 128/658 |
| 5,433,198 A | 7/1995 | Desai | 128/642 |
| 5,437,277 A | 8/1995 | Dumoulin et al. | 128/653.1 |
| 5,443,489 A | 8/1995 | Ben-haim | 607/115 |
| 5,450,846 A | 9/1995 | Goldreyer | 128/642 |
| 5,465,717 A | 11/1995 | Imran et al. | 128/642 |
| 5,471,982 A | 12/1995 | Edwards et al. | 128/642 |
| 5,471,988 A | 12/1995 | Fujio | 128/660.03 |
| 5,480,422 A | 1/1996 | Ben-Haim | 607/122 |
| 5,483,951 A | 1/1996 | Frassica et al. | 600/104 |
| 5,487,391 A | 1/1996 | Panescu | 128/699 |
| 5,538,008 A | 7/1996 | Crowe | 128/751 |
| 5,554,152 A | 9/1996 | Aita et al. | 606/7 |
| 5,555,883 A | 9/1996 | Avitall | 128/642 |
| 5,558,091 A | 9/1996 | Acker et al. | 128/653.1 |
| 5,558,092 A | 9/1996 | Unger et al. | 128/660.03 |
| 5,577,502 A | 11/1996 | Darrow et al. | 128/653.1 |
| 5,588,432 A | 12/1996 | Crowley | 128/660.03 |
| 5,617,857 A | 4/1997 | Chader et al. | 128/653.1 |
| 5,622,169 A | 4/1997 | Golden et al. | 128/653.1 |
| 5,715,822 A | 2/1998 | Watkins et al. | 128/653.5 |
| 5,729,129 A | 3/1998 | Acker | 324/207.12 |

FOREIGN PATENT DOCUMENTS

| | | |
|---|---|---|
| WO | WO 95/076957 | 3/1995 |
| WO | WO 95/09562 | 4/1995 |
| WO | WO 95/10226 | 4/1995 |
| WO | WO 95/19738 | 7/1995 |
| WO | WO 96/05768 | 2/1996 |
| WO | WO 96/41119 | 12/1996 |
| WO | WO 97/03609 | 2/1997 |
| WO | WO 97/29678 | 8/1997 |
| WO | WO 97/29679 | 8/1997 |
| WO | WO 97/29683 | 8/1997 |
| WO | WO 97/29684 | 8/1997 |
| WO | WO 97/29685 | 8/1997 |
| WO | WO 97/29701 | 8/1997 |
| WO | WO 97/29709 | 8/1997 |
| WO | WO 97/29710 | 8/1997 |
| WO | WO 97/29803 | 8/1997 |
| WO | WO 97/32179 | 9/1997 |

MEDICAL PROBES WITH FIELD TRANSDUCERS

CROSS-REFERENCE TO RELATED APPLICATIONS

The application is a 371 of PCT/US97/02443 filed Feb. 14, 1997 which claims benefit of Provisional Nos. 60/011,743, 60/011,723 both filed on Feb. 15, 1996 and Prov No. 60/017,635 filed May 17, 1996.

The following PCT applications, each of which names Biosense, Inc as an applicant are also incorporated by reference herein: Catheter Based Surgery filed on or about Feb. 14, 1997 in the Israeli Receiving Office; Intrabody Energy Focusing filed on or about Feb. 14, 1997 in the Israeli Receiving Office; Locatable Biopsy Needle, filed on or about Feb. 14, 1997 in the Israeli Receiving Office; Catheter Calibration and Usage Monitoring filed on or about Feb. 14, 1997 in the Israeli Receiving Office; Precise Position Determination of Endoscopes filed on or about Feb. 14, 1997 in the Israeli Receiving Office; Medical Procedures and Apparatus Using Intrabody Probes filed Feb. 14, 1997 in the United States Receiving Office; Catheter with Lumen filed Feb. 14, 1997 in the United States Receiving Office; Movable Transmit or Receive Coils for Location System filed Feb. 14, 1997 in the United States Receiving Office; and Independently Positionable Transducers for Location System filed Feb. 14, 1997 in the United States Receiving Office. The PCT application entitled, Multi-Element Energy Focusing, filed Feb. 14, 1996 in the Israeli Receiving Office and naming Victor Spivak as applicant is also incorporated by reference herein.

TECHNICAL FIELD

The present invention relates to medical probes having field transducers used for detecting the disposition of the probe, and to the medical procedures utilizing such probes.

BACKGROUND OF THE INVENTION

Conventional surgical procedures involve cutting through bodily structures to expose a lesion or organ within the body for treatment. Because these procedures create considerable trauma to the patient, physicians have developed minimally invasive procedures using probes inserted into the body. For example, devices commonly referred to as endoscopes include an elongated body having a distal end and a proximal end. The distal end of the probe body can be inserted into the gastrointestinal tract through a body orifice. The endoscope may be equipped with optical devices such as cameras or fiber optics to permit observation of the tissues surrounding the distal end, and surgery may be performed by inserting and maneuvering surgical instruments through a channel in the endoscope body. Other probes commonly referred to as laparoscopes and arthroscopes are inserted into the body through small holes formed in surrounding tissues to reach the bodily structures to be treated or measured. Still other probes, commonly referred to as catheters, can be advanced through the vascular system, as through a vein or artery, or through other bodily passages such as the urinary tract.

The physician can guide the probe to the desired location within the body by feel or by continuously imaging the probe and the body, as by fluoroscopy, during the procedure. Where the probe includes optical elements, the physician can guide the probe based on visual observation of the tissues surrounding the distal tip of the probe. However, this option is available only for probes such as conventional endoscopes which are large enough to accommodate the optical elements.

As described, for example, in U.S. Pat. Nos. 5,558,091, 5,391,199; 5,443,489; and in PCT International Publication WO 96/05768 Application PCT/US 95/01103, the disclosures of which are hereby incorporated by reference herein, the disposition of a probe—its position, orientation, or both—can be determined by using one or more field transducers such as a Hall effect or magnetoresistive device, coil or other antenna carried on the probe, typically at or adjacent the distal end of the probe, or at a precisely known location relative to the distal end of the probe. One or more additional field transducers disposed outside the body in an external frame of reference. The field transducers preferably are arranged to detect or transmit non-ionizing fields or field components such as a magnetic field, electromagnetic radiation or acoustical energy such as ultrasonic vibration. By transmitting the field between the external reference field transducers and the field transducers on the probe, characteristics of field transmission between these devices can be determined. The position and/or orientation of the field transducer, in the external frame of reference can be deduced from these transmission characteristics. As the field transducer is mounted to the probe, the position of the probe can be determined by determining the position of the field transducer in the external frame of reference. Because the field transducer allows determination of the position of the probe, such a transducer is also referred to as a "position sensor".

As described, for example, in the aforementioned U.S. Pat. No. 5,558,091, the frame of reference of the external field transducers can be registered with the frame of reference of imaging data such as magnetic resonance imaging data, computerized axial tomographic data, or conventional x-ray image data and hence the position and orientation data derived from the system can be displayed can as a representation of the probe superimposed on an image of the patient's body. The physician can use this information to guide the probe to the desired location within the patient's body, and to monitor its orientation during treatment or measurement of the body structure. This arrangement greatly enhances the ability of the physician to navigate the distal end of the probe through bodily structures. It offers significant advantages over conventional methods of navigating probes by feel alone. Because it does not require acquisition of an optical image of the surrounding tissues for navigation purposes, it can be used with probes which are too small to accommodate optical elements. The transducer-based system avoids the difficulties associated with navigation of a probe by continuous imaging of the probe and patient during the procedure. For example, it avoids exposure to ionizing radiation inherent in fluoroscopic systems.

However, still further improvements in transducer-based probe navigation and treatment systems would be desirable. In particular, it would be desirable to provide greater versatility in probe configurations. Thus, the diverse medical procedures require numerous different tools for use within the body. It would be desirable if any such tool could be guided and located in the same manner as the probes discussed above, without the need to adapt or redesign the tool to a accommodate the field transducer or position sensor. It would also be desirable to provide probes in diverse configurations matching different anatomical structures. Merely by way of example, it is sometimes desirable to advance a relatively stiff probe through anatomical structures defining a path having a particular radius of curvature unique to the patient. It is impractical to stock transducer-equipped probes in all of the various configurations required to accommodate different patients. Also, because field transducers can be impaired by exposure to certain sterilization processes, it would be desirable to provide single-use or limited-use field transducers which can be applied to an instrument.

DISCLOSURE OF INVENTION

The present invention addresses these and other needs.

One aspect of the present invention provides methods of configuring and operating a probe. A method according to this aspect of the invention preferably includes the steps providing a probe including a first field transducer and a probe body so that the field transducer is disposed in an arbitrary, user-selected disposition relative to a feature of the probe body, such as at an arbitrary disposition relative to the distal end of the probe body. The probe is calibrated by placing the aforesaid feature of the probe body at one or more known dispositions in the frame of reference defined by the external or reference field transducers of the system. While this feature of the probe body is in such known disposition, one or more calibration dispositions of the field transducer in the reference-transducer frame of reference is or are determined by transmitting one or more nonionizing fields between the first field transducer mounted on the probe body the reference field transducers and monitoring one or more characteristics of the fields at one or more of said transducers. The calibration process further includes the step of determining a transform between disposition of the first field transducer and disposition of said feature of said probe body from said one or more calibration dispositions and said one or more known dispositions. After the calibration steps, disposition of said feature of the probe is determined by (1) determining the disposition of the first field transducer by transmitting one or more non-ionizing fields between the first field transducer and said reference field transducers and monitoring one or more characteristics of the fields and (2) applying said transform to the so-determined disposition of the first field transducer.

Because the transform between disposition of the first field transducer and disposition of the probe body feature is determined during the calibration cycle, there is no need for any particular, predetermined spatial relationship between the first field transducer or position sensor and the distal end or other feature of the probe body to be tracked by the system during use. All that is required is that the spatial relationship remain fixed after calibration. Thus, according to this aspect of the invention, there is no need for any special configuration of the probe body; provided that the first field transducer or position sensor can be securely attached to a medical instrument of any type which can be inserted into the patient or contacted with the patient, that medical instrument can serve as an instrumented probe. This aspect of the invention allows the physician to use existing tools and to track the disposition of existing tools in the same manner as a specialized sensor-equipped probe.

The step of providing the probe can include the step of adjusting the probe body to a user-selected configuration, as by bending or otherwise deforming the probe body. In one preferred arrangement, the probe body includes a formable section which can be bent manually by the physician into a desired configuration after review of an image showing the relevant anatomical features, but which thereafter retains its shape. The probe is calibrated after bending. Thus, even if the sensor or first field transducer is mounted remote from the distal tip, the position of the distal tip can be tracked with sufficient accuracy to allow navigation of the tip through the anatomy. In effect, the physician can custom-form a probe as needed for any procedure. A further aspect of the present invention provides a pointing device or probes with a formable distal regions and with a field transducer or position sensor at the distal end, so that the position of the distal end can be monitored even without calibration as discussed above.

The known disposition used in the calibration cycle can be determined using the first field transducer, without the other elements of the probe, as by engaging the first field transducer with a fixed object in the external reference frame and determining disposition of the first field transducer.

A related aspect of the present invention provides components for use in a medical probe system. One component according to this aspect of the invention includes a field transducer as referred to above and a selectively operable mounting element adapted to secure the field transducer to a body of a medical instrument so that the disposition of the field transducer relative to the body of the instrument can be selected from among a range of dispositions. Preferably, such range includes all positions on the body; i.e., the mounting element can secure the field transducer anywhere on the instrument body. A component according to a further, related aspect of the invention includes the field transducer with a selectively operable mounting element adapted to secure the field transducer to any one of a plurality of different medical instruments having bodies of different configurations. In components according to these aspects of the invention, the mounting element may include an adhesive for bonding the field transducer to the instrument body, or else may include a clip attached to the field transducer, the clip being adapted to grip an instrument body.

The calibration steps can be repeated several times for a single feature of the probe body, using the same or different known dispositions and calibration dispositions, so as to enhance the accuracy of the calibration process. Alternatively or additionally, the calibration steps can be performed using more than one feature of a probe, so that a separate transform is developed for each feature. During use, the system can track all of the features for which such calibration steps were performed. For example, where a probe is bent to a user-defined shape, the calibration step can be performed for many points along the probe, and the system can display locations of these many points during use. Thus, the system can display a realistic depiction of the user-defined shape. A disposable device according to a further aspect of the invention includes a field transducer as discussed above, and a mounting element for securing the field transducer to a medical instrument, the mounting element being adapted to engage a body of the medical instrument so that said disposable device cannot be removed readily from the instrument without altering at least one feature of the disposable device. For example, the mounting element may be adapted to engage the instrument so that said device cannot be removed readily from the instrument without deforming or breaking a part of the mounting element. Devices according to related aspects of the invention incorporate the field transducer, a mounting element and a usage monitoring circuit element for recording use of the device. Thus, the usage monitoring circuit element may provide an indication representing the number of times the disposable device has been used or the total time the disposable device has been operatively used. These arrangements help to prevent improper reuse of the device.

The present invention will be better understood from the following detailed description of preferred embodiments of the invention, taken in conjunction with the accompanying drawings.

MODES FOR CARRYING OUT THE INVENTION

Figure 1:
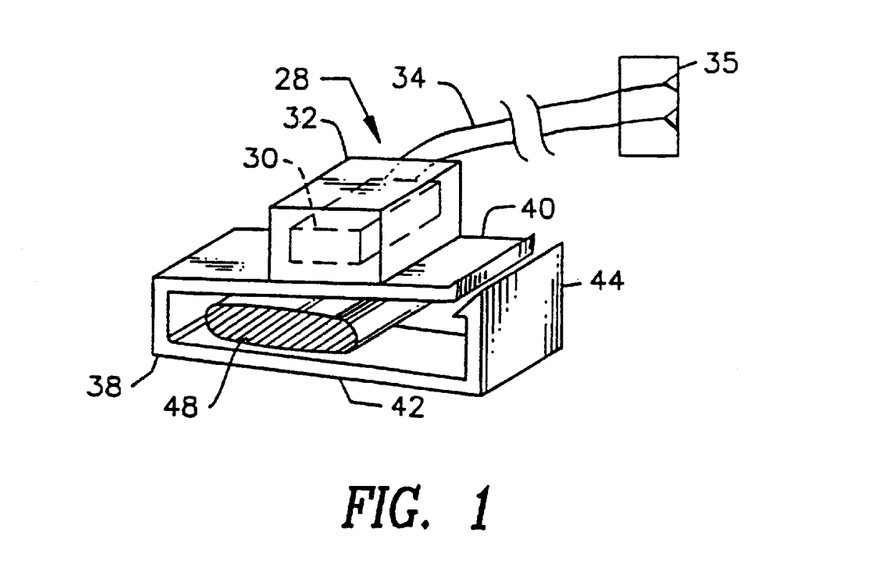
FIG. 1 is a diagrammatic perspective view depicting a device in accordance with one embodiment of the invention.

A disposable device in accordance with one embodiment of the invention includes a field transducer 30 permanently mounted in a body 32. Field transducer 30 is adapted to detect or radiate a non-ionizing field such as a magnetic, electromagnetic or acoustic field in such a manner that disposition of the field transducer can be at least partially determined from properties of the detected or radiated field. Field transducer or sensor 30 may be a multiaxis, solid-state position sensor of the type disclosed in U.S. Pat. No. 5,558,091. Such a multiaxis sensor includes a plurality of transducers sensitive to magnetic field components in mutually orthogonal directions. Other suitable field transducers or sensors include coils as disclosed in the aforementioned U.S. Pat. No. 5,391,199 and PCT International Publication WO 95/05768, incorporated by reference herein. The coils may be provided as a single coil having a single axis of sensitivity or as a plurality of mutually orthogonal coils capable of detecting electromagnetic field components in orthogonal directions. The sensor or field transducer 30 is provided with an appropriate cable 34 having a terminal block or plug 35.

Figure 2:
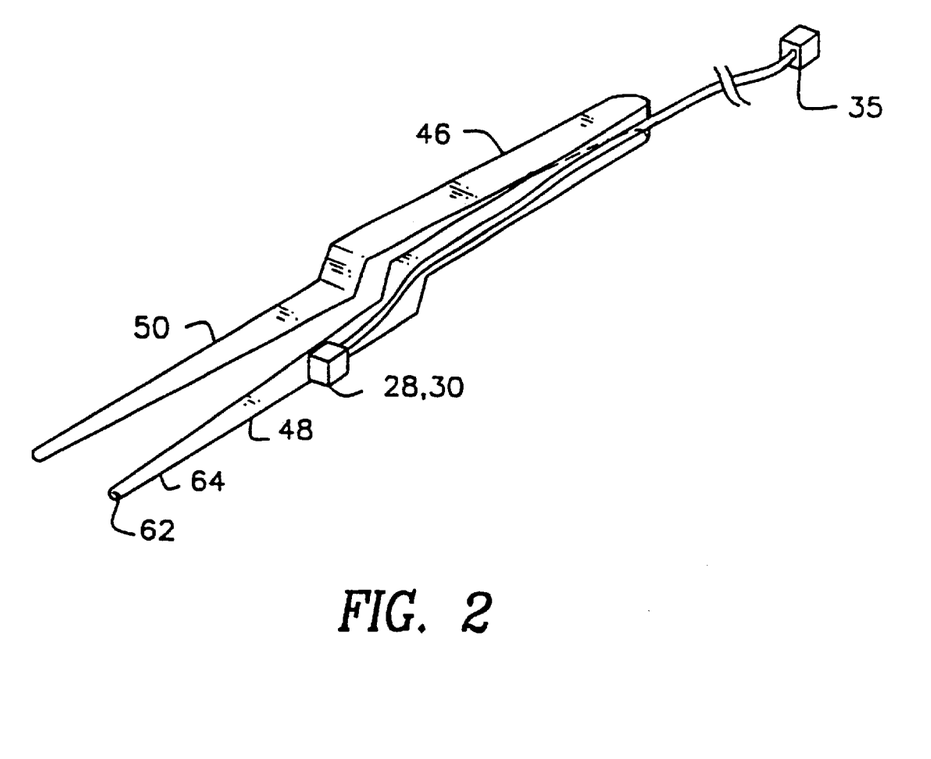
FIG. 2 is a diagrammatic perspective view depicting the device of FIG. 1 in conjunction with a medical instrument.

Body 30 is mechanically connected to or molded integrally with a polymeric clip 38. Clip 38 includes a pair of opposed legs 40 and 42 and a integral clasp 44 for holding the legs 40 and 42 in a closed position in which the legs are adjacent to one another. Clip 38 may be molded integrally with body 32 or else may be attached to the body by any suitable mechanical fastener, adhesive or bonding procedure. Clip 38 is adapted to encircle a part of a medical instrument or probe and grasp the encircled part between legs 40 and 42. For example, a conventional surgical forceps 46 has a pair of opposed elongated arms 48 and 50. Arm 48 can be grasped between opposed legs 40 and 42 of the clip. When clasp 44 is engaged with leg 40, legs 40 and 42 are forcibly engaged on opposite sides of arm 48 and tightly grip arm 48 so as to hold body 32, and hence field transducer or position sensor 30. Clip 38 is capable of engaging arm 48 at any point along its length selected by the user and of course is capable of engaging any other elongated implement which can be placed between legs 40 and 42.

The apparatus further includes a set of reference field transducers or antennas 52 (FIG. 3) mounted in a frame of reference external to the patient. For example, field transducers 52 may be mounted to a patient-supporting bed. Antennas 52 are linked to a field transmitting and receiving device 54 and a computer 56, which in turn is linked to a displayed device such as a cathode ray tube 58. These elements are arranged to cooperate with field transducer 30 or other movable field transducers or position sensors, to determine the dispositions of the movable field transducer in the frame of reference of the external field transducers or antennas. These elements of the apparatus can be as described in the aforementioned '091 or '199 patents. Other devices for detecting disposition of probes equipped with position sensors by transmission of non-ionizing fields are known in the art. As is known in the art, electromagnetic or magnetic fields can be transmitted between an antenna or field transducer mounted in a frame of reference and a movable position sensor or field transducer, and the disposition of the movable field transducer can be calculated from the characteristics of the transmitted. Thus, the external field transducers or antennas 52 and the movable position sensor or field transducer 30 cooperatively define a plurality of transmitter-receiver pairs. Each such pair includes one transmitter and one receiver as elements of the pair. One element of each such pair is disposed at an unknown disposition and the other element of each such pair is disposed at a known disposition in the external frame of reference. Typically, at least one element of each transmitter-receiver pair is disposed at a different position or orientation than the corresponding element of the other pairs. By detecting the characteristics of field transmission between elements of the various pairs, the system can deduce information concerning the disposition of the field transducer in the external frame of reference. The disposition information can include the position of the movable field transducer, the orientation of the movable field transducer or both.

Figure 3:
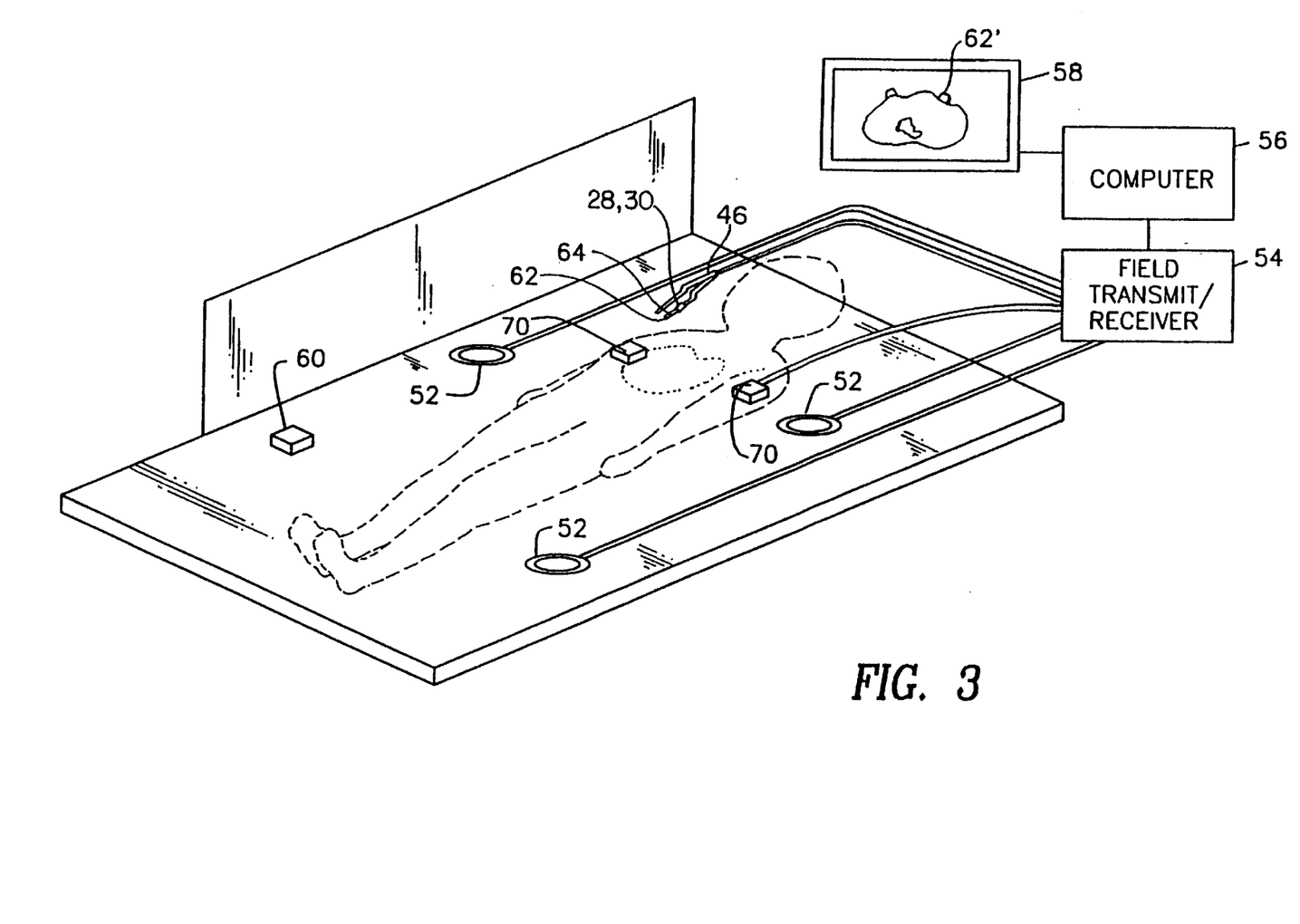
FIG. 3 is a further diagrammatic perspective view depicting the instrument and device of FIG. 1 and in conjunction with additional components and a medical patient.

In a method according to one embodiment of the invention, the physician first places device 28, and hence field transducer 30 at any convenient reproducible disposition within the frame of reference established by reference field transducers or antennas 52 as, for example, by abutting body 32 (FIG. 1) against some fixed object 60 in the vicinity of the reference of field transducers. Object 60 may be any object which does not interfere with a transmission of the fields as, for example, a non-magnetic object when electromagnetic fields are used. Object 60 need not be any specially configured or placed element. However, if desired object 60 may be especially configured to engage body 32 in a precise, reproducible manner as, for example, to engage a particular edge or feature of body 32.

Alternatively, object 60 may be configured so that it can be engaged by clip 38. In either case, device 28 and hence the movable field transducer or position sensor 30 is held in a fixed calibration or reference position and orientation. The field transmitting and receiving unit 54 and computer 56 are then actuated in the normal manner to determine the position and orientation of the movable or first field transducer 30 within device 28. In this step the system determines the position of object 60 in the frame of reference of reference field transducers or antennas 52 using device 28 and the first or movable field transducer 30. Thus, the position of object 60 is a known position. In particular, object 60 may include a tip, edge or hole, and the location of such tip edge or hole is known.

Device 28 is then attached to a medical instrument or probe 46 Musing clasp 38. A convenient feature of the instrument or probe to be tracked is selected by the physician. Such feature should be at a location on the instrument or probe which is rigidly connected to the location where device 28 is attached. For the particular forceps illustrated in FIG. 2, the feature to be tracked is the distal end 62 of the same arm 48 on which device 28 is mounted. The user then engages the preselected feature of the probe or instrument, such as distal tip 62 with fixed object 60 so as to place this feature of the instrument or probe 46 in a known position such as on the tip, edge or hole of object 60. That is, the feature 62 of the probe or instrument 46 is in the same known disposition as previously occupied by the first field transducer 30 and device 28. While the selected feature of the instrument is in this known disposition, the field transmit and receive unit is actuated once again to record a calibration disposition of first field transducer 30, i.e., the position and orientation of the first field transducer while tip 62 is disposed in engagement with object 60. Based on the calibration disposition of the first field transducer 30 and the known disposition of feature 62, the system calculates a transform between the position of first field transducer 30 and the position of feature or tip 62 on the instrument body.

Because arm 48 is a rigid body, there is a constant vector $V_p$ relating the position $P_p$ of the first field transducer 30 to the position $P_t$ of the tip or feature 62. The relationship is $$P_t = P_p + O_p^{-1} V_p \tag{1}$$

where $O_p$ is the orientation matrix defining the orientation of the first field transducer 30 in the frame of reference defined by reference transducers 52. When the tip or feature 62 is in the known position in engagement with object 60, $P_t = P_0$ where $P_0$ is the known position of feature 62, i.e., the position of object 60. Also, because the system determines the calibration disposition of first field transducer 30 in this condition, including both the position and orientation of the first field transducer, the values of $P_p$ and $O_p$ are also known. That is:

$$P_0 = P_1 + O_1^{-1} V_p \tag{2}$$

Where: $P_1$ represents the measured calibration position of the first field transducer in the calibration condition and $O_1$ represents the measured orientation of the first field transducer in the calibration condition. This equation is solved for vector $V_P$:

$$V_p = O_1 (P_0 - P_t) \tag{3}$$

The calculated value of $V_p$ represents a transform between position and orientation of the first field transducer 30 or device 28 and the position of feature 62 on the instrument body. At this point, the calibration cycle is complete. The calibration steps may be repeated while keeping tip or feature 62 in the same position, in engagement with object 60, but varying the orientation of the instrument body, so as to bring the first field transducer 30 to a new calibration disposition, such as a new position and orientation, and repeating the steps required to derive vector Vp from the new calibration disposition. Alternatively or additionally, the calibration steps may be repeated using one or more additional known positions of tip or feature 62. Thus, additional objects (not shown) may be provided at known positions within the frame of reference of the reference field transducers 52, and tip 62 may be engaged with each of these additional objects to establish an additional known position of the tip. While the tip is at each additional known position, the position and orientation of the first field transducer are recorded as discussed above to establish one or more additional calibration dispositions of the field transducer for each additional known disposition of tip 62. Here again, vector Vp is recalculated for each calibration disposition. The results of the various calculations can be combined with one another, to establish a best estimate for Vp. For example, Vp can be calculated by averaging the results for each component of the vector or, preferably, by selecting a vector value of Vp to yield the least mean square error with respect to the individually-calculated values. Additionally, the calibration can be tested by placing tip 62 on one or more additional known locations, such as on one or more additional objects, computing the position of the tip based upon the disposition of the field transducer and vector Vp, and then comparing the computed position and the known location. An alarm signal can be issued, or system operation can be inhibited, if the two locations differ by more than a preselected tolerance.

Following the calibration cycle, the system continues to monitor the position and orientation of the first field transducer 30 and hence of device 28. The system continually applies the transform or vector $V_p$ determined during the calibration cycle in equation (1), above, using new measured values of the position $P_p$ and orientation $O_p$ of the first field transducer 30 and thus determines the location $P_t$ of feature 62 in the frame of reference defined by reference transducers 52. This positional information can be treated in a known manner by computer 56 as, for example, to superpose a representation of feature 62 on image data showing a medical patient. As described, for example, in the aforementioned '091 patent, information concerning position and/or orientation of an object in the frame of reference defined by transducer 52 can be registered to the frame of reference of a previously acquired image using additional field transducers or position sensors 70. Thus, the system can display a representation 62' on display screen 58 in registry with the previously acquired image such as an MRI, CT or similar image. Alternatively, as described in U.S. Provisional Application No. 60/012,275 filed Feb. 26, 1996, the disclosure of which is incorporated by reference herein and as further described in copending, commonly assigned PCT Application entitled, Medical Procedures and Apparatus Using Intrabody Probes, filed of even date herewith and claiming priority from the aforesaid '275 Provisional Application, the disclosure of which is hereby also incorporated by reference herein, the information concerning position of feature 62 may be used to calculate the position of feature 62 relative to another probe advanced within the body and this information may be provided to the physician so that feature 62 can be guided or pointed toward such other probe.

A pseudocode description and accompanying algorithms are set forth in the appendix at the end of the present specification. Although the foregoing discussion provides for recovery of only the position of feature 62, and not its orientation, the orientation can be derived in the same manner. Thus, during the calibration cycle, the instrument can be held in a known orientation as, for example, by holding a known edge 64 of arm 48 in engagement with a particular face or feature of object 60. The computer can then calculate a direct transform between matrix $O_p$ defining the orientation of the first field transducer 30 and the orientation matrix defining the direction of edge 64 and hence defining the orientation of the probe or instrument 46. Here again, a calibration value $O_1$ for matrix $O_p$ is determined by measuring $O_p$ while the probe is in the known disposition and field transducer 34 is in the corresponding calibration disposition. Prior to this step, the known orientation of the face or feature of object 60 is established, as by measuring the orientation of device 28 while an edge of device body 32 is engaged with the face or feature of object 60.

The step of measuring the position and/or orientation of object 60 using device 28 may be omitted if the location of object 60 relative to reference transducers 52 is already known as, for example, where the object is supplied in a rigid unit with the transducers. Conversely, the location of object 60 may be measured using a different field transducer.

Figure 4:
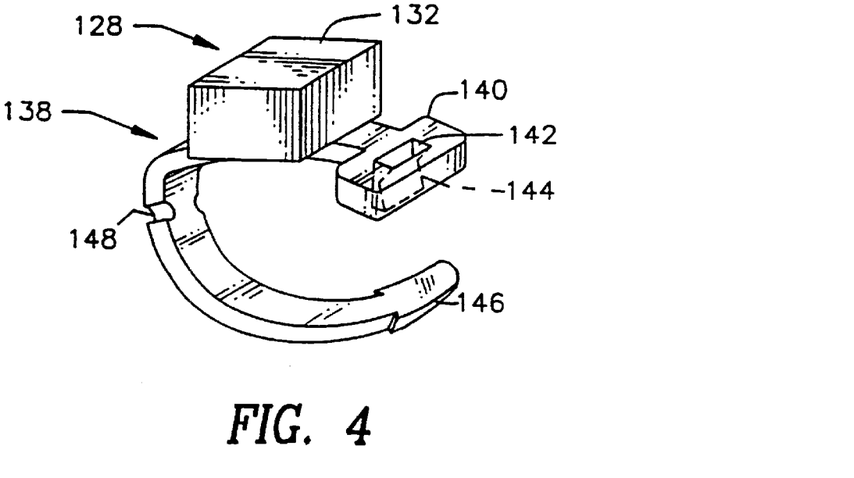
FIG. 4 is a further diagrammatic perspective view depicting a device in accordance with another embodiment of the invention.

A device 128 according to a further embodiment of the invention utilizes a clip or fastener 138 in the form of a flexible band generally similar to the bands used as cable ties in the electrical industry. For example, band 138 may be similar to the cable ties sold under the registered trademark TY-RAP by the Thomas & Betts Corporation of Memphis, Tenn., U.S.A. The band incorporates a head 140 with a hole 142. A locking barb 144 is disposed in head 140. The free end 146 of the band may be inserted through the hole and pulled past barb 144, whereupon the barb locks the free end in place and prevents its retraction out of the hole. This band may serve to lock the body 132 of the device to the instrument or probe. Once the band is tightened around the probe or instrument, it is difficult or impossible to remove or move the device from the tool and free the band for engagement with another instrument. A relatively weak, frangible section 148 may be provided along the length of the band so that the user can remove the device from an instrument after use. However, because the band is broken during removal, it is apparent to any subsequent user that the device has already been used. Even if the band can be slid off the end of the instrument without breaking the band, it will still be apparent to the user that the device has been used, because the band will remain engaged in head 140.

Figure 5:
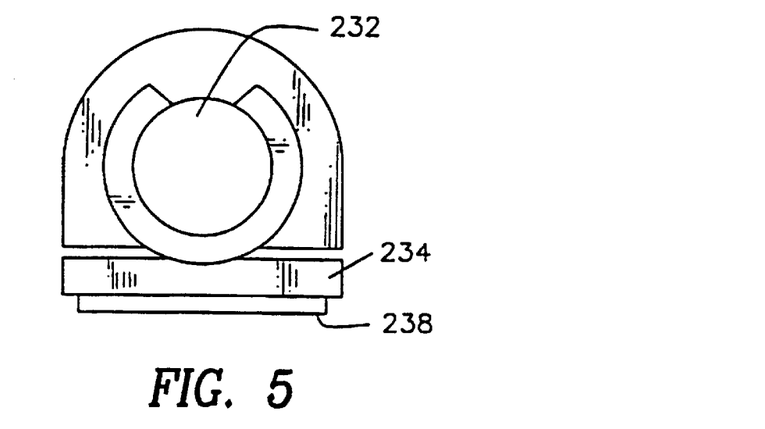
FIG. 5 is a diagrammatic end elevational view depicting components in accordance with a further embodiment of the invention.
Figure 6:
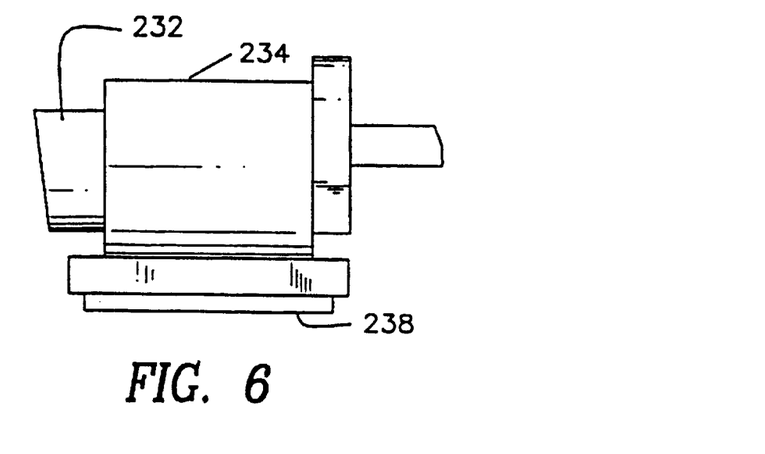
FIG. 6 is a diagrammatic side elevational view depicting the components of FIG. 5.

As depicted in FIGS. 5 and 6, the attachment between the body 232 holding a field transducer and instrument or tool may include an adhesive 238. Body 232 is engaged with an intermediate element or clip 234, which in turn bears a layer of a relatively strong adhesive. Body 232 may be either removably attached to intermediate clip 234 or permanently mounted thereto.

Figure 7:
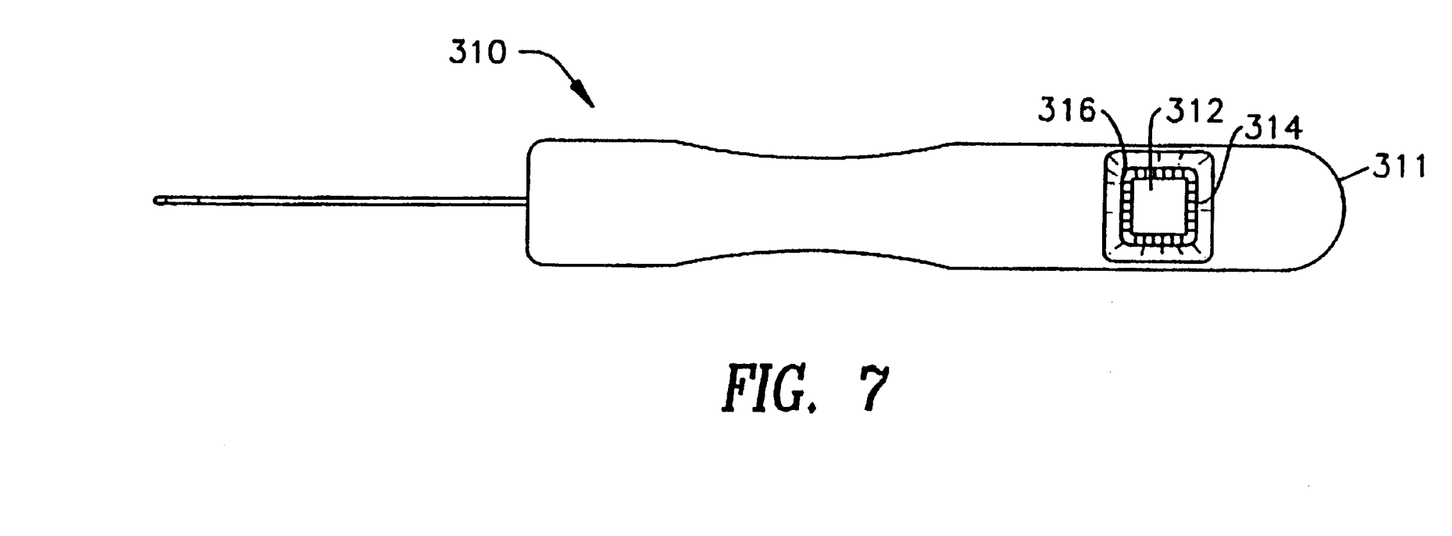
FIG. 7 is a schematic, top view, illustration of a surgical instrument having mounted thereon a disposable device, in accordance with a further embodiment of the present invention.
Figure 8:
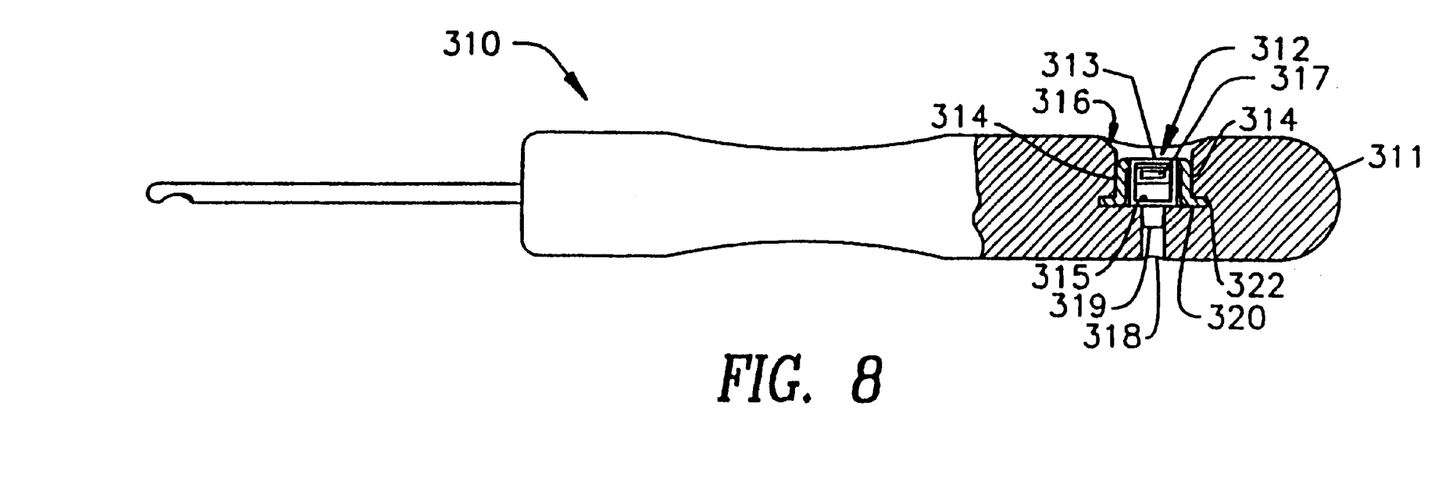
FIG. 8 is a schematic, partly cross-sectional, side-view, illustration of the surgical instrument of FIG. 7.

A surgical instrument 310 and disposable device 312 in accordance with another embodiment of the present invention are depicted in FIGS. 7 and 8. Instrument 310 may include any surgical and/or diagnostic instrument as is known in the art, for example, a scalpel as shown or a forceps discussed above. Device 312 includes a body 313, which encapsulates the field transducer 315. Body 312 is provided with resilient appendages 314 having externally bent ends 320. Appendages 314 are preferably spaced from body 313, when no force is applied to the appendages, so that ends 320 can be displaced inwardly towards body 313 when appendages 314.

Device 312 is preferably installed in a cavity 316 formed in a preselected portion, for example a handle 311, of instrument 310. Cavity 316 is preferably slightly larger than device 312. As shown in FIG. 8, cavity 316 preferably includes circumferential extensions 322 which are adapted to accommodate bent ends 320 of appendages 314 when device 312 is fully inserted into cavity 316, as shown in the drawings. Cavity 316 further includes an access extension 318 which enables access to cavity 316 from a direction opposite to the direction from which device 312 is installed. Extension 318 is considerably narrower than body 313 of device 312. Body 313 is provided with features which closely fit to the features of handle 311, so that body 313 will be disposed in a precise, repeatable location on instrument 310, in precise, known registration with respect to the blade of the instrument. For example, body 313 may include a projection 319 which fits closely within access opening 318. Thus, the field transducer 315 will be located at a known disposition with respect to other features of the instrument, such as the distal tip or blade. In this embodiment, the calibration steps discussed above are not required. However, such steps may be performed to check that device 312 is properly mounted, or to provide better precision.

To install device 312 in cavity 316, appendages 314 are urged against body 313, allowing body 313 to be pushed into cavity 316 together with bent ends 320. For example, cavity 316 may have a "lead-in" or inclined ramp surfaces surrounding its open side. As body 313 is pushed into the cavity, ends 320 ride are forced inwardly toward body 313 by the inclined surfaces. When bent ends 320 reach circumferential extensions 322, appendages 314 spring back to their original condition and, thus, ends 320 arelocked in extensions 322. It should be appreciated that, once ends 320 are locked in extensions 322, device 312 cannot be readily uninstalled, i.e., removed from cavity 316, because appendages 314 cannot be readily urged against body 313. When ends 320 of appendages 314 are securely locked in extensions 322, device 312 is firmly mounted in cavity 316, body 313 is precisely and securely located relative to instrument 310.

To remove device 312, a rigid, narrow, member (not shown) is inserted via access extension 318 and forcefully pushed against the projection 319 of body 313. Since ends 320 are securely locked by extensions 322, device 312 cannot be removed with appendages 314 intact. Appendages 314 and ends 320 are designed to break off body 313 when the force exerted on body 313 exceeds a predetermined threshold. Once appendages 314 are broken off body 313 and device 312 is removed, the device cannot be securely installed as described above. Thus, once removed, device 312 must be replaced with a new, unused device 312, thereby preventing re-use of the device.

Additionally or alternatively, device 312 may include a circuit element, e.g. a single conductor, which is adapted to be physically or electrically damaged during forced removal of device 312 from cavity 316. The electrical connection associated with device 312 may be arranged to connect such conductor in series with a testing circuit in the reusable elements of the system as, for example, in field transmitting and receiving unit 54 (FIG. 3). The testing circuit may inhibit operation of the system or issue a warning signal if the circuit element is damaged. Alternatively, the device may be arranged so that the field transducer itself is damaged and rendered inoperative during removal of device 312 from cavity 316. In these arrangements, disposable device 312 cannot be removed readily from instrument 310 readily without altering the device in some manner which renders it unusable. It should be appreciated that absolute assurance against removal without alteration is not required. All that is required is that the normal, convenient process for removing disposable device cause the alteration. For example, in the arrangement of FIGS. 7 and 8, a skilled person determined to defeat the system may be able to disengage ends 320 by careful work using a tool inserted between appendages 314 and the cavity wall. However, the system is still effective to prevent reuse as the vast majority of users will use the normal removal process.

The physical configuration of the device can be altered to allow reuse of device 312. For example, ends 320 may be omitted or may be shaped to allow disengagement without breakage. Device 312 may include a usage monitoring element 317, e.g. an electronic key, as described, for example, in commonly assigned U.S. Provisional Patent Application No. 60/011723, filed Feb. 15, 1996, in commonly assigned U.S. Provisional Patent Application No. 60/017635, filed May 17, 1996, and in U.S. Pat. No. 5,383,874, the disclosures of which are incorporated herein by reference. Device 317 may include a non-volatile memory or other electronic circuit element bearing information relating to the usage of device 312. Element 317 is also connected to the reusable components of the system by the same electrical connector which connects field transducer 315 to the system. The reusable system may increment a count maintained by circuit element 317 each time device 312 is connected, so that the circuit element maintains a count of the number of times device 312 has been used. Alternatively or additionally, the reusable system may increment a count stored in element 317 periodically while the device is connected, so that element 317 maintains a record of total usage time. The reusable system may be arranged to inhibit use when the usage count exceeds a specified value. Element 317 may store other information specific to device 312, such as a serial number and/or lot number identifying the device, calibration data and the like.

Device 312 also may be arranged to interact with the instrument in other ways, so that the device "reads" information from the instrument pertinent to operation of the system. For example, where the same device may be engaged with a plurality of different instruments, the device may read identifying information on the instrument and convey that information to the position sensing system. For example, device 312 may be equipped with switches or exposed contacts which engage corresponding elements of the device; different types of devices, or different individual devices, may be equipped with devices to trip these different switches or connect to different exposed contacts, thereby providing an electrical code indicative of the device. Other conventional optical, mechanical or electrical code-reading devices can be used. The device information can indicate a particular device shape (for a rigid device) or can convey information defining the degree of rigidity of the device, the distance from a predefined transducer mounting location to the tip of the device, or other information about characteristics of the device which may influence the precision of the system. For example, in a system using magnetic fields, the device information may specify a particular device as bearing magnetic material and thus indicate to the system that the position-determining accuracy of the system will be lower than normal.

The particular physical designs of mating elements are merely exemplary. In the embodiments discussed above, the connection between the device incorporating the first field transducer (the device mounted on the instrument) and the rest of the position detecting system is made through a hard-wired connection with a plug. Such a hard-wired connection can be replaced by a radio, infrared or other wireless telemetry link, in which case the device desirably includes an independent power supply such as a battery. Telemetry avoids the physical encumbrance of loose wires trailing from the instrument. Alternatively, if wires are used, they can be secured to the instrument, as by tape, clips or adhesive. Numerous other combinations of features are known in the art of disposable medical instrument design for locking mating parts together. Features such as snaps, latches, bayonet locks, screw threads and the like can be employed. In the embodiment of FIGS. 7 and 8, the resilient elements are formed on the body of the disposable device. However, the reverse arrangement, where the handle or other part of the reusable device, incorporates resilient parts, can also be utilized. A handle as illustrated in FIGS. 7 and 8 may be configured so that the handle can be releasably associated with other portions of the instrument, such as an elongated rod or tube for insertion into the body.

In some preferred embodiments of the present invention, the disposable device includes a field transducer or position sensor adapted for multiple, yet controlled, use. In these preferred embodiments of the invention, the instrument and the position sensor are sterilized separately and, after sterilization, the position sensor is removably mounted on the mounting site of the instrument. After the instrument has been used, the position marker is removed without being altered. Such multiple-use position sensors may be used in a system in which each position sensor is assigned to a specified surgical/diagnostic instrument or a specified type of surgical/diagnostic instrument. In some preferred embodiments, the position sensor may includes identifying circuitry as discussed above, and the system may be arranged to allow operation of each position sensor only in conjunction with the specified instrument or type of instrument. Additionally or alternatively, the position sensor mounting on the instrument may have a shape unique to the specified instrument or type of instrument. Each position sensor is uniquely shaped to be mountable only on the instrument to which the marker is assigned.

Figure 9:
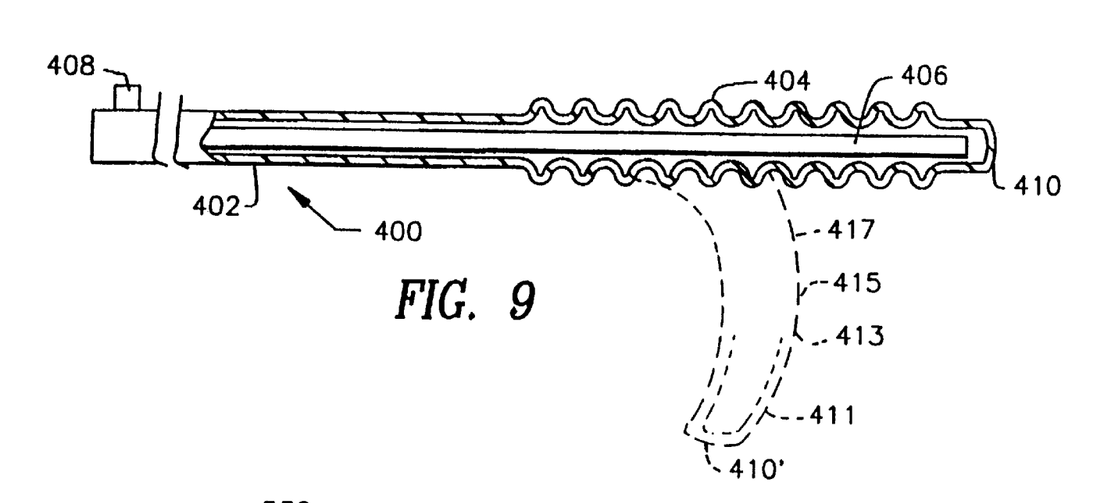
FIG. 9 is a diagrammatic sectional view depicting apparatus in accordance with a further embodiment of the invention.

An instrument in accordance with another embodiment of the invention includes an elongated probe body 400 (FIG. 9) having a relatively rigid proximal portion and a formable region 404. Formable region 404 is arranged so that the user can bend it to the desired shape and so that after bending, the formable region will substantially retain its new shape. In the embodiment illustrated, the formable region includes a corrugated polymeric covering and an internal reinforcing wire which can be plastically deformed. Wire 406 may be formed from a relatively soft metal having a "dead-bend" or non-resilient characteristic. Merely by way of example, annealed aluminum and soft alloys such as common solders and other lead-based alloys, silver solders and others have outstanding dead-bend characteristics. Metals having some resilience also can be employed. Instrument 400 further includes a field transducer or position sensor 408 mounted on proximal portion 402. In operation, the physician can deform formable region 404 to a shape required to accommodate anatomical structures of a particular patient, typically by reviewing images of the anatomical structures such as CT, X-ray or MRI images. This process brings the distal tip 410 of the instrument body to an arbitrary, user-selected location 410' with respect to position sensor or field transducer 408. The instrument is then calibrated as described above, to establish the vector between transducer 408 and tip location 410'. Provided that the configuration of the formable section does not change during use, the system can accurately track the location of tip 410. insert C Thus, the formable section should be rigid enough to retain its shape after forming. Stated another way, the forces applied to bend the formable section deliberately are substantially greater than the forces encountered by the formable section during use in the patient's body.

The calibration process can be repeated for numerous points along the bent probe as, for example, at each of points 411, 413, 415, and 417, in addition to the tip 410'. For example, each of these features or points along the bent probe can be engaged with the object of known location (60, FIG. 3) while a calibration disposition of first field transducer 408 is acquired. Thus, the system acquires a vector or transform relating the position of each of the additional points to the position and orientation of field transducer 408. In use, the system displays representations of each of these additional points, as well as a representation of tip 410', on the display 58 (FIG. 3). The system thus displays a multipoint curve representing the shape of the probe during use. Where a large number of features are calibrated in this manner, the system can display an image of the arbitrarily-shaped probe approximating a silhouette of the probe. This image can be superposed on the previously-acquired patient image, as discussed above with reference to a single point representation. A similar approach can be used to obtain a silhouette of a non-formable tool such as a single arm of the forceps of FIG. 2. However, if the geometry of a non-formable tool with reference is known in advance, as from stored data defining the geometry of the tool, the vectors for all points on the tool can be deduced from the vector for a single point established as above. For example, the position vector from first field transducer 30 to any point along forceps arm 48 can be deduced from the vector Vp from the first field transducer 30 to tip 62, discussed above, and known data defining the shape of arm 48. The computer system may store a library of tool shapes and select a tool shape for use in such computation based on input from the user. In a variant of the probe depicted in FIG. 9, the position sensor is disposed at tip 410, so that calibration is not required, and deformation of the formable section during use will not affect positioning accuracy. However, this requires that the probe be of adequate diameter to accommodate the position sensor.

Probes having formable sections can be used in a wide variety of procedures, but are particularly useful in procedures involving the brain. When the probe is in a generally J-shaped configuration as shown in broken lines in FIG. 9, it can inserted between the brain and the dura through a craniotomy to reach around the hippocampus. A further useful neurosurgical procedure in accordance with the present invention utilizes a probe having a long, flaccid flexible region such as a thin rubber tube, and a position sensor at the distal end of such flexible region. For example, the flexible region may be a tube of a soft silicone rubber or other soft polymer of about 2 mm diameter of less. The flexible region is threaded between the brain and dura of a mammalian subject such as a human patient. If the probe encounters an obstacle, the physician can continue to urge the probe in the distal or threading direction. Even if the soft, flexible region kinks, it will not damage the brain. This procedure allows the physician to probe obstacles with confidence. It is particularly useful during operations to install cortical electrode strips during epilepsy mapping.

Figure 10:
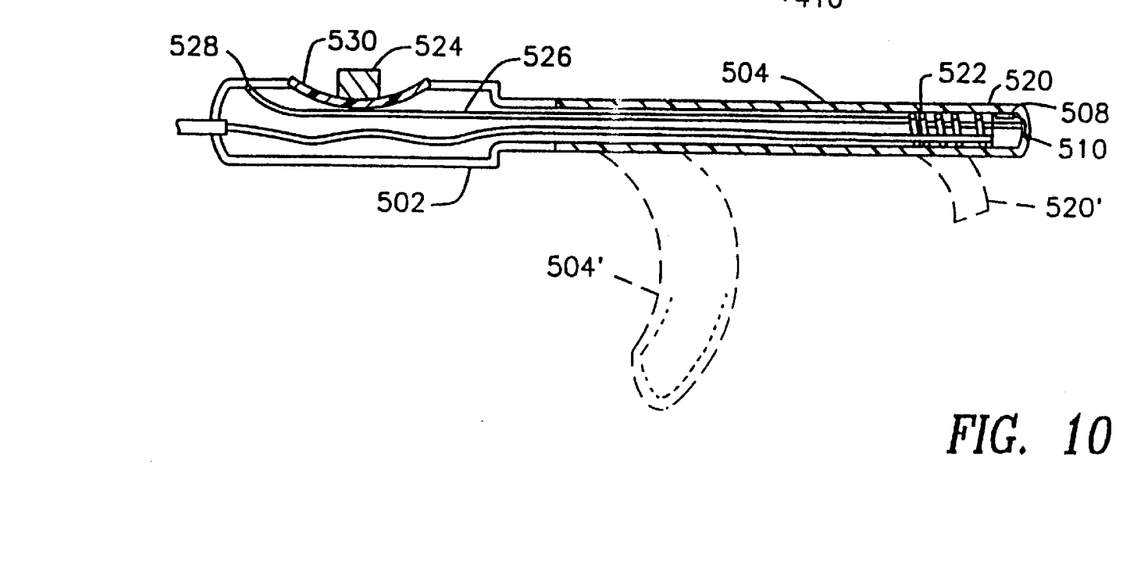
FIG. 10 is a diagrammatic sectional view depicting apparatus in accordance with yet another embodiment of the invention.

A probe in accordance with a further embodiment of the invention includes a rigid proximal portion 502 and formable portion 504 as discussed above with reference to FIG. 9, and further includes a flexible region 520 at the distal end of the probe. Region 520 is considerably more flexible than formable portion 504. For example, region 520 may include a soft, supple polymeric tube, such as a thin tube of a soft silicone rubber. Region 520 optionally may include a spring 522 to provide resilience. A steering mechanism is provided which allows the user to control the shape of flexible region 520. In the particular arrangement illustrated, the steering mechanism includes an actuator button 524 movably mounted to the proximal region 502 and a cable 526 extending within the probe from a fixed end 528 adjacent button 524 to a point in flexible region 520 adjacent the distal end 510 of the probe. By pressing button 524 inwardly, the user can pull on cable 526 and thus bend flexible region 520 as depicted in broken lines at 520'. A spring 530 biases button 524 away from cable 526, so that the flexible region tends to return to the position illustrated in solid, lines in FIG. 10. Other devices are known in the art for selectively bending the distal end of a probe using control inputs supplied at the proximal end, and those devices can be used in the device of FIG. 10. Formable region 504 can be manually bent as shown in broken lines at 504.' A field transducer 508 is mounted in flexible region 520 and provided with leads extending to the proximal end of the probe for connection to the position monitoring system. Probes as discussed above with reference to FIG. 10 can be used to control the configuration of a flexible endoscope. When the probe is inserted into the working channel of the endoscope, the distal end of the endoscope will bend along with the distal end of the probe. In a variant of the probe depicted in FIG. 10, formable region 504 can be omitted, and the flexible region 520 may be joined directly to the distal end of a rigid proximal portion. Such a probe can be used with a rigid endoscope; the rigid section of the probe is positioned within the rigid endoscope, whereas the flexible region protrudes from the distal tip of the endoscope.

Figure 11:
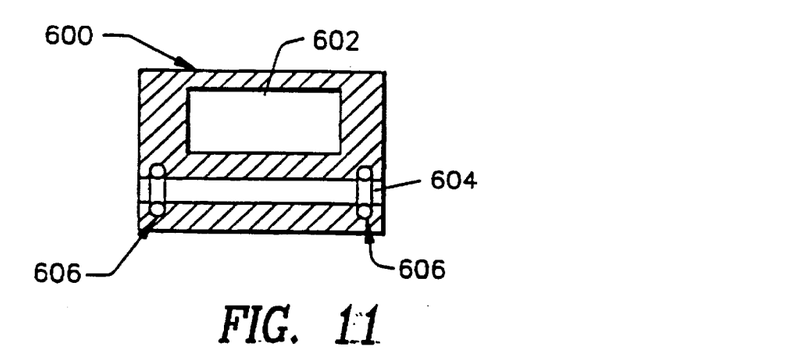
FIG. 11 is a diagrammatic sectional view depicting apparatus in accordance with a further embodiment of the invention.

As shown in FIG. 11, a device in accordance with another embodiment of the invention includes a body 600 housing a field transducer or position sensor 602. Body 600 has a lumen 604 with a pair of resilient O-rings 606 mounted therein. In use, the body can be mounted on an elongated instrument such as a biopsy needle by advancing the needle through lumen 604, thereby frictionally engaging the needle with O-rings 606. A unit of this type typically is provided in sterile condition, so that it does not contaminate the biopsy needle or other instrument. For example, the device may be provided in a sterile overwrap and the needle may be thrust through the sterile overwrap into lumen 604. The entire body 600, including O-rings 606, can be provided as a single integral elastic unit. In a further variant, the elastic component can be replaced by a shrinkable tube so that the disposable device, with the position sensor or field transducer thereon, can be attached to a medical instrument by shrinking the tube around a part of the instrument. Such a shrinkable tube may be a heat-shrinkable tube of the type commonly used in the electrical industry, or may be shrinkable by chemical action. Where the disposable device is to be mounted on a portion of the instrument which will be advanced into the patient during use, such as on or adjacent the distal end of a needle, the field transducer or position sensor desirably is a compact unit such as a lithographically-formed coil or set of coils. A preferred lithographic coil has a size of 0.8 mm wide by 3 mm long, a thickness of 0.3 mm and includes a rectangular coil having the following characteristics: a line width of $6\mu$, a line spacing of $6\mu$ and a line thickness of $2\mu$. The number of windings is preferably the maximum number which fit in the coil. A thin (0.3 mm) ferrite layer may be provided adjacent the coil to increase its sensitivity. The coil may be formed on a silicon substrate, or preferably, on a flexible polyimide substrate which can conform to the needle. Preferably, more than one layer of conduction lines is provided. The use of sensor-equipped biopsy needles, and other probes, are described in greater detail in co-pending, commonly assigned PCT Application entitled LOCATABLE BIOPSY NEEDLE, filed of even date herewith, the disclosure of which is hereby incorporated by reference herein.

Figure 12:
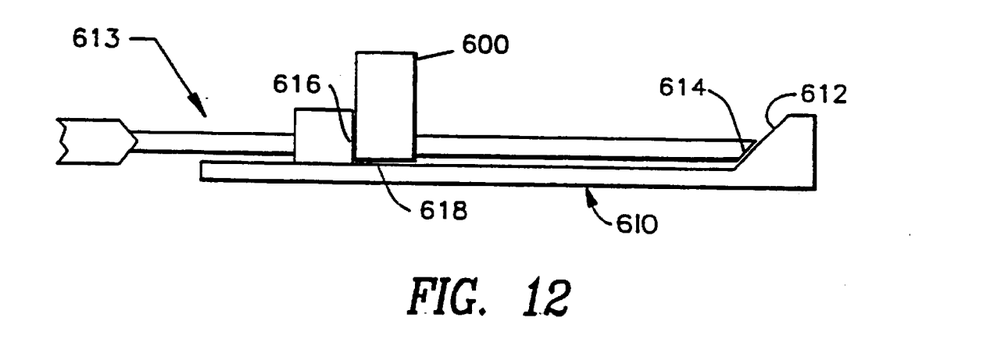
FIG. 12 is a diagrammatic elevational view depicting the apparatus of FIG. 11 in conjunction with a medical instrument.
Figure 13:
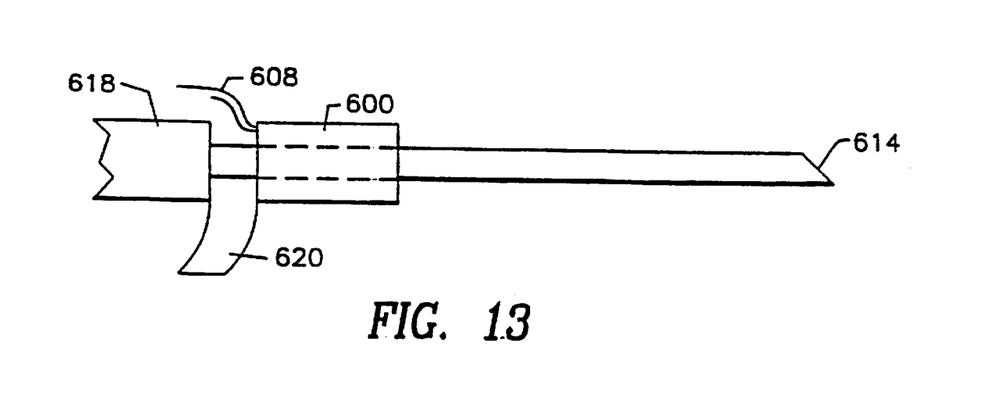
FIG. 13 is a diagrammatic view depicting the apparatus of FIG. 11 in conjunction with another medical instrument.

As depicted in FIG. 12, a jig 610 can be used to position a disposable device having a field transducer or position sensor thereon in a predetermined disposition relative to a feature of an instrument or probe. Thus, jig 610 has a surface 612 for engaging the bevel 614 of a biopsy needle 613, and surfaces 616 and 618 for engaging surfaces of a disposable device 600, such as surfaces of the disposable device body 602. The instrument or biopsy needle 613 is positioned temporarily in the jig, with the bevel 614 engaging surface 612 of the jig, and the disposable device is brought into engagement with surfaces 616 and 618, thereby positioning body 602 at a predetermined position and orientation with respect to bevel 614. Such jig-based positioning can be used as an alternative to the calibration process discussed above. In a further alternative, the body 600 of the disposable device carrying the field transducer or position sensor is brought to a known position relative to the feature to be tracked, such as bevel 614, by abutting the disposable device body 600 against another feature of the instrument, such as the hub 618 of the needle, which is located at a known position relative to feature 614. A tool 620 of known dimensions may be interposed between the disposable device body and feature 618. Other jigs may be used for instruments of different configurations.

It will be appreciated by persons skilled in the art that the present invention is not limited to what has been thus far described. Rather, the scope of the present invention is limited only by the claims.

INDUSTRIAL APPLICABILITY

The invention can be used in medical and related procedures.

```
APPENDIX
acquire position p_o:
acquire position p_1 and orientation o_1;
call function attache_findVec to get v_p;
while using tool {
        acquire probe position p_p and orientation o_p;
        call function attach_convertPos;
3) Code for function attach_findVec, attach_convertPos
        The following is the C code of the implementation of the tool
calibration algorithm:
        Function attach_findVec is to find vector v_p by using v_p = o_1
(p_o - p_1)
        Function attach_convertsPos is to use v_p to find tool tip
position by using p_1 = p_p + o_p^-1 v_p
void    attach_findVec(pos_in_1, pos_ref, ori_in_1, pos_vec)
double pos_in_1[3];    /* probe location reading when placing tip of
                          the attached tool at the absolute location
                          reference
                  point  in  mapping  space    */
double pos_ref[3];     /* probe location reading when placing tip of
                          the probe at the absolute location reference
                          point in mapping space */
double ori_in_1 [3] [3]; /* probe orientation matrix when placing tip of
                          the attached tool at the absolute location
                          reference point in mapping space, i.e., the
                          orientation associated with pos_in_1 [3]; the
                          matrix should be normalized and orthogonal */
```

```
-continued
double pos_vec [3];    /* resulted constant vector of tool calibration
                          that is going to be used for calculating tool tip
                          position */
(
        int i;
        double difference [3];
        for (i = 0; i < 3; i --)
        difference [i] = pos_ref [i] = pos_in_1 [i];
        pos_vec [0] =       ori_in_1 [0] [0; = difference [0] =
                            ori_in_1 [0] [1] = difference [1] =
                            ori_in_1 [0] [2] difference [2] =
        pos vec [1] =       ori_in_1 [1] [0] = difference [0] =
                            ori_in_1 [1] [1] = difference [1] =
                            ori_in_1 [1] [2] = difference [2];
        pos_vec [2] =       ori_in_1 [2] [0] = difference [0] =
                            ori_in_1 [2] [1] = difference [1] =
                            ori_in_1 [2] [2] = difference [2];
void    attach_convertPos (pos_in, pos_out, ori_vec, pos_vec)
double pos_in [3];     /* the location vector reading of the probe
                          attached to the tool */
double pos_out [3];    /* the converted location which reflects the tool
                          tip position after returning of this routine */
double ori_vec [3] [3]; /* the orientation matrix reading of the probe
                          attached to the tool; the matrix should be
                          normalized and orthogonal */
double pos_vec [3];    /* the constant vector from tool calibration
                          procedure, i.e., the resulted vector from routine
                          attach_findVec */
int i, j;
double ori_vec_rev [3] [3];
/* find the reverse of the matrix ori_vec */
for (i = 0; i < 3; i --)
        for (j = 0; j < 3; j --) (
                ori_vec_rev [i] [j] = ori_vec [j] [i];
)
pos_out [0] = pos_in [0]         = ori_vec_rev [0] [0] = pos_vec [0]
                                 = ori_vec_rev [0] [1] = pos_vec [1]
                                 = ori_vec_rev [0] [2] = pos_vec [2];
pos_out [1] = pos_in [1]         = ori_vec_rev [1] [0] = pos_vec [0]
                                 = ori_vec_rev [1] [1] = pos_vec [1]
                                 = ori_vec_rev [1] [2] = pos_vec [2];
pos_out [2] = pos_in [2]         = ori_vec_rev [2] [0] = pos_vec [0]
                                 = ori_vec_rev [2] [1] = pos_vec [1]
```

What is claimed is:

1. A component for use in a medical probe system having at least one of a plurality of different medical instruments, the component comprising:
    (a) a body;
    (b) a field transducer connected to the body for detecting or radiating a non-ionizing field so that the disposition of the field transducer can be at least partially determined from properties of such field;
    (c) a selectively operable mounting element for securing the body and the field transducer to any one of a plurality of different medical instruments having different configurations, wherein when the body and the field transducer are secured to any one of the instruments, a position of the field transducer is calibrated with respect to a pre-selected feature of the any one of the instruments; and
    (d) an electrical circuit element connected to the body for bearing information relating to the usage of the any one of the instruments having the body and the field transducer attached thereto.

2. A component as claimed in claim 1 wherein said mounting element includes an adhesive for bonding the field transducer to the pre-selected feature of the any one of the instruments.

3. A component as claimed in claim 1 wherein said mounting element includes a clip attached to the field transducer for gripping an instrument portion to thereby mechanically connect the field transducer to the instrument portion.

4. A disposable device for mounting to a medical instrument, the disposable device comprising:
   (a) a body;
   (b) a field transducer connected to the body for detecting or radiating a non-ionizing field so that the disposition of the field transducer can be at least partially determined from properties of such field;
   (c) a mounting element for securing the body and the field transducer to a medical instrument, said mounting element including a band for engaging a portion of a medical instrument, wherein said mounting element allows a position of the field transducer to be calibrated; and
   (d) an electrical circuit element connected to the body for bearing information relating to the usage of the medical instrument.

5. A device as claimed in claim 4 wherein said mounting element can alter said electrical circuit element.

6. A device as claimed in claim 5 wherein said electrical circuit element constitutes a part of said field transducer.

7. A device as claimed in claim 6 wherein said mounting element includes features having a predetermined configuration for engaging a feature of the instrument so as to support the field transducer in a predetermined disposition relative to the instrument.

8. A disposable device according to claim 7 wherein said body has at least one appendage.

9. A disposable device for mounting to a medical instrument, the disposable device comprising:
   (a) a body;
   (b) a field transducer for detecting or radiating a non-ionizing field so that the disposition of the field transducer can be at least partially determined from properties of such field, wherein a position of the field transducer is calibrated with respect to a pre-selected feature on the medical instrument when the field transducer is secured to the pre-selected feature on the medical instrument;
   (c) a mounting element for securing the field transducer and the body to the medical instrument; and
   (d) an electrical circuit element bearing information specific to the field transducer.

10. A device according to claim 9 wherein said electrical circuit element bears calibration information related to the disposable device.

11. A device as claimed in claim 9 wherein said electrical circuit element bears information identifying the disposable device.

12. A device as claimed in claim 9 wherein said electrical circuit element bears information indicating whether the disposable device has been used.

* * * * *